United States Patent [19]

Mano

[11] 4,304,010
[45] Dec. 8, 1981

[54] TUBULAR POLYTETRAFLUOROETHYLENE PROSTHESIS WITH POROUS ELASTOMER COATING

[75] Inventor: Hiroshi Mano, Osaka, Japan

[73] Assignee: Sumitomo Electric Industries, Ltd., Osaka, Japan

[21] Appl. No.: 84,324

[22] Filed: Oct. 12, 1979

[51] Int. Cl.³ .............................................. A61F 1/24
[52] U.S. Cl. ............................................... 3/1.4; 3/1
[58] Field of Search ......................................... 3/1, 1.4

[56] References Cited

U.S. PATENT DOCUMENTS

| 3,279,996 | 10/1966 | Long, Jr. et al. | 3/1 V X |
| 3,479,670 | 11/1969 | Medell | 3/1.4 |
| 3,585,647 | 6/1971 | Gajewski et al. | 3/1.4 |
| 4,011,861 | 3/1977 | Enger | 3/1 X |
| 4,208,745 | 6/1980 | Okita | 3/1 X |

FOREIGN PATENT DOCUMENTS 562278  9/1977  U.S.S.R. .................. 3/1.4

Primary Examiner—Clifford D. Crowder
Attorney, Agent, or Firm—Sughrue, Mion, Zinn, Macpeak and Seas

[57] ABSTRACT

A tubular prosthesis comprising a porous tubing of polytetrafluoroethylene having a micro structure composed of fibers and nodes connected to one another by said fibers, said fibers being radially distributed, and a porous coating on the outside surface of said polytetrafluoroethylene tubing and a process for producing the same is disclosed.

15 Claims, 1 Drawing Figure

TUBULAR POLYTETRAFLUOROETHYLENE PROSTHESIS WITH POROUS ELASTOMER COATING

BACKGROUND OF THE INVENTION

1. Field of the Invention

This invention relates to an improvement in and relating to a tubular organic prosthesis composed of a porous tubing of polytetrafluoroethylene (to be abbreviated "PTFE"), and is directed to increasing the strength of the tubing and its ability to connect with the tissues of patients.

2. Description of the Prior Art

Many reports have been made heretofore to show that a porous tubing of PTFE produced by a stretching method can be clinically used as a tubular organic prosthesis, especially as a vascular prosthesis. Such a prosthesis is regarded as better than conventional prostheses made of knitted or woven fabrics. A PTFE tubing which has been subjected to a stretching treatment has a microstructure composed of very fine fibers and nodes connected to one another by the fibers. The diameters of the fibers vary depending on stretching conditions, and can be made much smaller than those of the fibers of the knitted or woven fabrics mentioned above. Moreover, since the pore diameter and porosity of the tubing can be varied freely, when it is used, for example, as an artificial vessel, it is pliable and scarcely permits formation of thrombus. The tubing also shows good formation of a pseudointima on the inner surface without any appreciable adverse effect on the surrounding tissues. Thus, the stretched PTFE tubing is regarded as one of the best tubular organic prostheses.

The stretched PTFE tubing, however, has the disadvantage that when it is used as a tubular organic prosthesis and joined with the living body the needle or suture tends to tear the tubing. This tearing frequently occurs in the axial direction of the porous PTFE tubing. Since this is due to the orientation of the fine PTFE fibers formed as a result of stretching, it can be reduced to some extent by biaxially stretching the tubing, namely stretching it in the axial direction and expanding its diameter, thereby to change the structure of the fine fibers to a radial orientation. A great improvement in strength, however, cannot be expected from this process alone. Furthermore, it is difficult for natural occlusion of suture holes to occur based on the elasticity of the porous PTFE tubing alone, and when used as an artificial vessel, bleeding from the suture holes is also a problem.

The present invention offers a solution to these problems in a junction operation.

SUMMARY OF THE INVENTION

It is an object of this invention to provide a tubular organic prosthesis composed of a biaxially oriented porous tubing of polytetrafluoroethylene and a porous coating of an elastomer connected to its outside surface.

Another object of this invention is to provide a tubular organic prosthesis which permits easy entry and attachment of the surrounding tissues to promote the assimilation of the prosthesis.

According to this invention, there is provided a tubular organic prosthesis comprising a porous tubing of polytetrafluoroethylene having a microstructure composed of fibers and nodes connected to one another by said fibers, said fibers being radially distributed, and a porous coating of an elastomer bound to the outside surface of said polytetrafluoroethylene tubing.

DETAILED DESCRIPTION OF THE INVENTION

Figure 1:
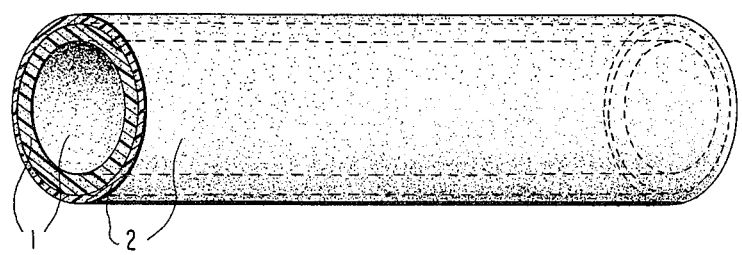
FIG. 1 is a side view of the tubular prosthesis showing the essential elements thereof. Said tubular prosthesis is provided with a body of porous PTFE 1, which body is provided with an elastomeric coating upon its outer surface 2.

As a result of providing a porous elastomer coating on its outside surface, the porous PTFE tubing of the present invention does not undergo tearing by a joining needle or suture. This also has the advantage that in a junction operation, the suture holes are occluded by the elasticity of the porous elastomer coating. Moreover, the porous elastomer coating permits easy entry and connection of the surrounding tissues of a patient, and thus promotes the assimilation of the porous PTFE tubing as an organic prosthesis.

The porous tubing of PTFE in accordance with this invention is produced by the method described in Japanese Patent Publication No. 13560/67 and, e.g., U.S. Pat. Nos. 3,953,566 and 3,962,153. A liquid lubricant is mixed with an unsintered powder of PTFE, and the mixture is extruded into a tubular form by a ram-type extruder. The PTFE used in this invention preferably has a molecular weight of $10^6$ to $10^7$. The tubing is stretched biaxially after the liquid lubricant is optionally removed from it. Preferably the tubing is stretched in the axial direction, and its diameter is expanded. The tubing is heated at a temperature above about 327° C. which is the sintering temperature while fixing it in place to avoid shrinkage. Thus, the stretched and expanded structure is fixed and a tubing having increased strength is obtained. The resulting porous PTFE tubing has a microstructure composed of very fine fibers and nodes connected to one another by these fibers. Because the diameters and lengths of these fibers and the sizes and number of the nodes can be varied depending upon the stretching and sintering conditions, the pore diameter and porosity of the resulting porous tubing can be determined freely. It has been clinically confirmed that when this tubing is used as a vascular prosthesis, it suitably has an average pore diameter of about 2 μm to about 100 μm, a porosity of at least 70%, and a wall thickness of 0.3 to 1.0 mm.

In the microstructure of the porous PTFE tubing used in this invention, the fibers are distributed not unidirectionally but radially. This fibrous structure is obtained by biaxially stretching the PTFE tubing, namely by stretching it in the axial direction and expanding its diameter. Expansion of its diameter can be achieved by reducing the pressure on the outside surface of the tubing, or pressing its inside surface, or simultaneously performing these two procedures while heating. Alternatively, the diameter of the tubing may be mechanically enlarged by passing an article of a suitable configuration through the inside of the tubing. Stretching of the tubing in the axial direction and expansion of its diameter are carried out simultaneously or successively, or may be carried out simultaneously with the final sintering step. The porous PTFE tubing obtained by biaxial stretching is more pliable and less prone to longitudinal tearing than a porous PTFE tubing stretched only in the axial direction because the fibers are distributed not only in the axial direction but radially in all directions. However, to perform a junction operation using this biaxially stretched porous PTFE tubing more improvements in strength, natural occlusion of the suture holes and the ability to connect with the tissues of a patient are desired.

A porous elastomer coating is provided on the outside surface of the porous PTFE tubing in accordance with this invention in order to solve the aforesaid problems.

Any elastomer can be used in this invention which is not harmful to the body. Examples are fluorine rubber, silicone rubber, urethane rubber, acrylic rubber, and natural rubber. Usually, elastomers are used in a crosslinked state and in this invention as well the elastomers are preferably crosslinked in order to prevent their deterioration in the body.

Preferably the elastomer coating used in the present invention provides a prosthesis having a suture tear resistance of at least 350 g/ply.

The porous elastomer coating in accordance with this invention is described in detail below with reference to a crosslinked fluorine rubber as a typical example. Substantially the same description will apply to other elastomers.

Examples of the fluorine rubber are a vinylidene fluoride/hexafluoropropylene copolymer, a vinylidene fluoride/chlorotrifluoroethylene copolymer, and a tetrafluoroethylene/propylene copolymer. A fluorine rubber is compounded with an acid acceptor, a crosslinking agent, and if desired, a filler before crosslinking. Examples of the acid acceptor are magnesium oxide and calcium oxide, and examples of the crosslinking agent are aliphatic polyamine derivatives, organic peroxides, and isocyanates. A typical compounding recipe consists of 100 parts by weight of a vinylidene fluoride/hexafluoropropylene copolymer, 15 parts of magnesium oxide, and 0.5 to 3 parts by weight of an aliphatic polyamine derivative.

A porous coating of the elastomer can be formed on the outside surface of the porous PTFE tubing by a variety of methods including a method comprising wrapping a separately prepared porous sheet of the elastomer about the outside surface of the tubing and bonding it, a method comprising coating a solution of an elastomer compound containing a blowing agent on the outside surface of the tubing and then decomposing the blowing agent, a method comprising coating a solution of an elastomer compound having a soluble substance dispersed therein on the outside surface of the tubing and dissolving the soluble substance to form a porous structure, a method comprising dissolving an elastomer compound in a mixture of a solvent and a nonsolvent, coating the solution on the outside surface of the tubing and drying the coating to render it porous, or a method comprising coating a solution of an elastomer compound on the outside surface of the tubing and removing the residual solvent by dipping the coated tubing in a nonsolvent bath or heating it to a temperature above the boiling point of the solvent, thereby to render the coating porous.

The present invention further provides a method for forming a porous coating of an elastomer, which comprises coating the outside surface of a porous tubing of PTFE with a solution of an elastomer compound or a liquid elastomer compound, and before drying the elastomer coating, applying a negative pressure to the inside wall of the porous tubing with a gas or liquid whereupon passing through the elastomer the gas or liquid foams the elastomer and renders the coating porous (The term "negative pressure" as referred to herein is a pressure which is greater at the inside wall of the tubing than the outside wall).

Thus, another aspect of this invention is a process for producing a tubular organic prosthesis, which comprises coating the outside surface of a porous tubing of polytetrafluoroethylene with a solution of an elastomer compound or a liquid elastomer compound; before drying the elastomer, applying a negative pressure to the inside wall of the porous tubing to foam said elastomer; and crosslinking the elastomer to form a porous coating of the elastomer on the outside surface of the tubing, the porous tubing being obtained by forming a mixture of unsintered polytetrafluoroethylene and a liquid lubricant into a tubular form, and biaxially stretching the tubing and sintering it. To render the elastomer porous a pressure of usually about 0.05 to 1 kg/cm$^2$ is applied by means of a gas or liquid to the inside wall of the PTFE tubing. A preferred viscosity of the elastomeric coating before foaming is from about 100 to about 5,000 c.p. at 25° C.

According to the process of this invention, a porous elastomer coating having a relatively large pore diameter can be formed easily, and its pore diameter can be made larger than the pore diameter of the porous tubing of PTFE. Advantageously, the pores can be obtained in an open cellular structure. This is desirable from the standpoint of the ability of the resulting product to connect with the tissues of a patient when it is used as an organic prosthesis. When the organic prosthesis of this invention is used as an artificial vessel, a suitable average pore diameter of the porous elastomer coating is in the range of about 10 μm to about 500 μm. It has been confirmed that pore sizes within this range can be easily obtained by the process of this invention. In a preferred embodiment of the present invention the elastomer is a fluorine rubber and the elastomer coating is 20 to 500 μm thick and has a porosity in the range of 50% to 90%.

When the elastomer is a fluorine rubber, ketones and esters are suitable as a solvent therefor. If required, a diluent such as aliphatic or aromatic hydrocarbons and alcohols may be used to provide a suitable solution viscosity for coating.

The thickness of the porous elastomer coating which suits the objects of this invention is equal to or smaller than the wall thickness of the porous PTFE tubing and is usually about 20 to 500 μm. Suitable thicknesses can be obtained by adjusting the viscosity of the coating solution.

The elastomer coating is then dried, and crosslinked. If the crosslinking agent, etc., necessary for this step are incorporated in the coated elastomer solution, the final product can be obtained by placing the resulting structure in an atmosphere having suitable crosslinking conditions. The fluorine rubber is crosslinked by heating in the air or in steam to provide a porous PTFE tubing having bonded thereto a porous elastomer coating with superior durability.

The radially distributed microfiber structure of the porous PTFE tubing in accordance with this invention has the advantage that the longitudinal tearing of the PTFE tubing is substantially inhibited, and the porous elastomer coating is firmly bonded to the porous PTFE tubing. The greatest characteristic feature of this invention lies in a combination of the porous PTFE tubing having such a microstructure with the porous elastomer coating. The porous PTFE tubing and the porous elastomer coating are bonded to each other as a result of a part of the elastomer entering the pore spaces of the PTFE tubing. If the fibers of the microstructure of the porous PTFE tubing are distributed only in the axial direction of the tubing, the porous elastomer coating is susceptible to peeling along this direction, and a high bond strength cannot be obtained. In contrast, since the porous PTFE tubing in accordance with this invention has a microfibrous structure having radially distributed fibers, the porous elastomer coating does not peel off in one direction, and the elastomer easily enters the pore spaces of the porous PTFE tubing. As a result, the elastomer coating is bonded to the PTFE tubing with a high bond strength which cannot be obtained in the prior art.

The tubular organic prosthesis of this invention is very useful as an artificial vessel, but can also be used for the prosthesis of other tubular organs including the esophagus, trachea, biliary duct, ureter, and urethra.

The following Examples illustrate the present invention more specifically. It should be understood that the scope of the invention is not limited by these Examples.

EXAMPLE 1

One hundred parts by weight of fine PTFE powder, Polyflon F-104 (a trademark for a product of Daikin Kogyo Co., Ltd.), was mixed uniformly with 29 parts by weight of a liquid lubricant (Deobase). The mixture was pre-formed under pressure, and extruded by a ram-type extruder into a tubing having an inside diameter of 3.0 mm and an outside diameter of 4.5 mm. The tubing was dipped in trichloroethylene to extract and remove the liquid lubricant, and then stretched 200% in the axial direction of the tubing while it was heated at about 250° C. The stretched tubing was heated at 350° C. while reducing the pressure on the outside surface of the tubing to expand its diameter and simultaneously sinter the tubing. The tubing obtained was a porous tubing having an inside diameter of 4.0 mm, and outside diameter of 4.9 mm, and a porosity of 79%.

Separately, 100 parts by weight of a fluorine rubber (Viton A-35, a product of Du Pont) was compounded with 15 parts by weight of magnesium oxide (Kyowa Mag MA-30, a product of Kyowa Chemical Industry Co., Ltd.) and 1.5 parts by weight of hexamethylenediamine carbamate. The resulting compound was dissolved in methyl ethyl ketone to form a 30% solution. The solution was coated on the outside surface of the porous PTFE tubing, and pressurized air at 0.3 kg/cm$^2$ was blown into the inside of the tubing and through the fluorine rubber layer. The tubing was dried at 50° C. in the air to remove the methyl ethyl ketone, and then heated at 150° C. for 30 minutes. Then, the temperature was gradually raised, and finally, the tubing was heated for 24 hours in a circulating air current at 200° C. to form a porous crosslinked fluorine rubber coating having a thickness of 0.3 mm. The resulting coated tubing was pliable and flexible.

When a stainless steel wire having a diameter of 0.40 mm was inserted in a loop-like configuration into the wall of the tubing at 5 mm from one end of the tubing, and pulled in the axial direction of the tubing at a speed of 50 mm/min., tearing occurred in the tubing under a load of 1,220 g which was far larger than the load (180 g) under which tearing occurred in the porous PTFE tubing before provision of the porous fluorine rubber coating. Holes left after inserting a surgical suturing needle were closed naturally under the elasticity of the fluorine rubber. Thus, the resulting product had various superior characteristics as a tubular organic prosthesis.

EXAMPLE 2

A porous PTFE tubing having an inside diameter of 6.0 mm, an outside diameter of 7.0 mm and a porosity of 76% was produced by the same method as in Example 1. Separately, 100 parts by weight of the same fluorine rubber compound as used in Example 1 was dissolved in 300 parts by weight of acetone. Furthermore, a mixture of 10 parts by weight of water and 150 parts by weight of isopropyl alcohol which was a nonsolvent for the fluorine rubber was added, and they were mixed with stirring. The resulting solution was coated on the outside surface of the porous PTFE tubing, and dried in the air at 25° C. to render the fluorine rubber layer porous. The product was heated at 150° C. for 30 minutes. The temperature was gradually raised, and finally, it was heated for 24 hours in a circulating air current at 200° C. to form a porous crosslinked fluorine rubber coating having a thickness of 0.05 mm. The load under which tearing occurred in the coated tubing was 870 g. Thus, the product had superior characteristics as a tubular organic prosthesis.

While the invention has been described in detail and with reference to specific embodiments thereof, it will be apparent to one skilled in the art that various changes and modifications can be made therein without departing from the spirit and scope thereof.

What is claimed is:

1. A tubular organic prosthesis comprising a porous tubing of polytetrafluoroethylene having a microstructure composed of fibers and nodes connected to one another by said fibers, said fibers being radially distributed, and a porous coating of an elastomer bound to the outside surface of said polytetrafluoroethylene tubing.

2. The tubular organic prosthesis of claim 1, wherein said elastomer is selected from the group consisting of fluorine rubber, silicone rubber, urethane rubber, acrylic rubber and natural rubber.

3. The tubular organic prosthesis of claim 1, wherein said elastomer is crosslinked.

4. The tubular organic prosthesis of claim 1 having a suture tear resistance of at least 350 g/ply.

5. The tubular organic prosthesis of claim 1, wherein said elastomer is a fluorine rubber selected from the group consisting of vinylidene fluoride/hexafluoropropylene copolymer, vinylidene fluoride/chlorotrifluoroethylene copolymer and tetrafluoroethylene/propylene copolymer.

6. The tubular organic prosthesis of claim 5 having a suture tear resistance of at least 350 g/ply.

7. The tubular organic prosthesis of claim 1, wherein said elastomeric coating has a porosity of about 50% to 90%.

8. The tubular organic prosthesis of claim 1, wherein said elastomeric coating is about 20 to 500 μm thick.

9. The tubular organic prosthesis of claim 1, wherein said elastomeric coating is prepared by coating a liquid elastomer or a solution of an elastomer on the outside surface of said porous tubing and applying a negative pressure to the inside wall of said tubing to thereby render the elastomeric coating porous.

10. The tubular organic prosthesis of claim 9 having a suture tear resistance of at least 350 g/ply.

11. The tubular organic prosthesis of claim 1, wherein said tubular organic prosthesis is a vascular prosthesis.

12. The tubular organic prosthesis of claim 11 having a suture tear resistance of at least 350 g/ply.

13. The tubular organic prosthesis of claim 1, wherein said PTFE tubing has an average pore diameter of at least 2 μm, a porosity of at least about 70% and a wall thickness of about 0.3 to 1.0 mm.

14. The tubular organic prosthesis of claim 13, wherein said elastomer is a fluorine rubber selected from the group consisting of vinylidene fluoride/hexafluoropropylene copolymer, vinylidene fluoride/chlorotrifluoroethylene copolymer and tetrafluoroethylene/propylene copolymer.

15. The tubular organic prosthesis of claim 14 having a suture tear resistance of at least 350 g/ply.

* * * * *

UNITED STATES PATENT AND TRADEMARK OFFICE
CERTIFICATE OF CORRECTION

PATENT NO. : 4,304,010
DATED : December 8, 1981
INVENTOR(S) : Hiroshi Mano

It is certified that error appears in the above—identified patent and that said Letters Patent is hereby corrected as shown below:

On the face of the patent, between lines [22] and [51], insert --[30] Foreign Application Priority Date October 12, 1978 [J] Japan ...............53-125952--.

Signed and Sealed this

Sixth Day of April 1982

[SEAL]

Attest:

GERALD J. MOSSINGHOFF

*Attesting Officer*    *Commissioner of Patents and Trademarks*